(12) United States Patent
Ryan et al.

(10) Patent No.: US 8,700,431 B2
(45) Date of Patent: Apr. 15, 2014

(54) CARE PLAN CHANGE PROPAGATION

(75) Inventors: John C. Ryan, Boston, MA (US);
Yaqiong (Jade) Fang, Milpitas, CA (US)

(73) Assignee: Koninklijke Philips N.V., Eindhoven (NL)

( * ) Notice: Subject to any disclaimer, the term of this patent is extended or adjusted under 35 U.S.C. 154(b) by 339 days.

(21) Appl. No.: 12/446,981

(22) PCT Filed: Oct. 31, 2007

(86) PCT No.: PCT/US2007/083079
§ 371 (c)(1),
(2), (4) Date: Apr. 24, 2009

(87) PCT Pub. No.: WO2008/060854
PCT Pub. Date: May 22, 2008

(65) Prior Publication Data
US 2010/0017228 A1    Jan. 21, 2010

Related U.S. Application Data

(60) Provisional application No. 60/865,041, filed on Nov. 9, 2006.

(51) Int. Cl.
*G06Q 50/22*    (2012.01)
*G06Q 10/10*    (2012.01)
*G06F 19/00*    (2011.01)
(52) U.S. Cl.
CPC ............... *G06Q 50/22* (2013.01); *G06Q 10/10* (2013.01); *G06F 19/30* (2013.01)
USPC ............................................................ 705/3

(58) Field of Classification Search
CPC ......... G06Q 50/22; G06Q 10/10; G06F 19/30
USPC ................ 705/3; 434/236, 262, 365; 706/14; 707/9
See application file for complete search history.

(56) References Cited

U.S. PATENT DOCUMENTS

| | | |
|---|---|---|
| 5,265,010 A | 11/1993 | Evans-Paganelli et al. |
| 5,879,163 A | 3/1999 | Brown et al. |
| 5,887,133 A | 3/1999 | Brown et al. |
| 5,897,493 A | 4/1999 | Brown |
| 5,951,300 A * | 9/1999 | Brown .......................... 434/236 |

(Continued)

FOREIGN PATENT DOCUMENTS

| | | |
|---|---|---|
| JP | 2002297771 A | 10/2002 |
| WO | 0078374 A1 | 12/2000 |
| WO | 0225551 A1 | 3/2002 |

*Primary Examiner* — John Pauls

(57) ABSTRACT

In a medical health care network (10) for providing individualized health care programming to many patients, a method and apparatus for updating the programming is described. When a patient is new to the system, a health care professional takes a generic care plan template (26) and fills it in with the patient's specific health information. A care plan scheduler (36), using a completed template (26), assigns content for the patient to experience. When new content becomes available, the health care professional notes it on the template (26). The scheduler (36) then looks for all instances of the old content and replaces it with the new content in the most seamless way possible. A content replacement database (40) interprets old data in light of the new content so that the old data does not become misleading or obsolete.

13 Claims, 2 Drawing Sheets

(56) References Cited

U.S. PATENT DOCUMENTS

| | | |
|---|---|---|
| 5,960,403 A | 9/1999 | Brown |
| 5,997,476 A | 12/1999 | Brown |
| 6,101,478 A | 8/2000 | Brown |
| 6,168,563 B1 | 1/2001 | Brown |
| 6,248,065 B1 | 6/2001 | Brown |
| 6,290,646 B1 | 9/2001 | Cosentino et al. |
| 6,375,469 B1 | 4/2002 | Brown |
| 6,454,705 B1 | 9/2002 | Cosentino et al. |
| 6,723,045 B2 | 4/2004 | Cosentino et al. |
| 6,755,783 B2 | 6/2004 | Cosentino et al. |
| 6,968,375 B1 | 11/2005 | Brown |
| 2002/0133377 A1 | 9/2002 | Brown |
| 2002/0188182 A1 | 12/2002 | Haines et al. |
| 2003/0014279 A1 | 1/2003 | Roman et al. |
| 2003/0069753 A1 | 4/2003 | Brown |
| 2003/0163351 A1 | 8/2003 | Brown et al. |
| 2003/0233253 A1 | 12/2003 | Peth et al. |
| 2004/0019259 A1 | 1/2004 | Brown et al. |
| 2004/0102685 A1 | 5/2004 | Cosentino et al. |
| 2004/0117207 A1 | 6/2004 | Brown |
| 2004/0117208 A1 | 6/2004 | Brown |
| 2004/0117209 A1 | 6/2004 | Brown |
| 2004/0219500 A1 | 11/2004 | Brown et al. |
| 2005/0026131 A1* | 2/2005 | Elzinga et al. ........... 434/365 |
| 2005/0027562 A1 | 2/2005 | Brown |
| 2005/0043060 A1 | 2/2005 | Brandenberg et al. |
| 2005/0080652 A1 | 4/2005 | Brown |
| 2005/0086083 A1 | 4/2005 | Brown |
| 2005/0172021 A1 | 8/2005 | Brown |
| 2005/0172022 A1 | 8/2005 | Brown |
| 2005/0228883 A1 | 10/2005 | Brown |
| 2005/0235060 A1 | 10/2005 | Brown |
| 2005/0273509 A1 | 12/2005 | Brown |
| 2006/0004611 A1 | 1/2006 | Brown |
| 2006/0015017 A1 | 1/2006 | Cosentino et al. |
| 2006/0080152 A1 | 4/2006 | Brown |
| 2006/0089969 A1 | 4/2006 | Brown et al. |
| 2006/0100910 A1 | 5/2006 | Brown |
| 2006/0167735 A1 | 7/2006 | Ward |
| 2007/0100829 A1* | 5/2007 | Allen et al. ........... 707/9 |
| 2008/0126277 A1* | 5/2008 | Williams et al. ........... 706/14 |
| 2008/0268413 A1* | 10/2008 | Leichner ........... 434/262 |

* cited by examiner

CARE PLAN CHANGE PROPAGATION

The present application relates to ongoing health care for patients with chronic illnesses or long term medical conditions. More specifically, the present application is directed to a secure, personalized platform service that connects patients to their care team. In order to provide patients the best available treatment and care, as information and technology advances, so too should data made available to patients advance.

Patients who have chronic or ongoing healthcare issues often have lifestyle issues which complicate the medical issues. For example, diabetes can be aggravated by diet, lack of exercise, obesity, and the like. One system for helping these patients to manage their disease, adjust their lifestyle, and the like, provides each patient with personalized programming. The patient is provided with a care plan that manifests itself in a series of educational or motivational programs directed to their specific healthcare issues. For example, the patient might be provided with educational and motivational programming at the same time each day to assist the patient in establishing and maintaining a diet and exercise regimen. The programming is provided on disc, from a programming memory, or from a central source, such as the hospital or medical care facility that has prescribed the programming and travels over a public communications network to the patient's home. There, a set top box decodes the signals intended for the specific patient and displays them on the patient's television, and the patient can interact with the programming using their TV or set top box remote. The set top box provides for user feedback, such as weigh-ins, blood pressure readings, and the like, to be communicated from the patient to the healthcare facility.

Although such systems are successful, medical knowledge and disease care tactics are ever increasing in quality. Health care professionals desire to provide their patients with the latest information and methods of treatment available. With new technologies and processes, there is an inevitable learning curve that organizations experience and benefit from. As organizations collect more experience in the field, they develop strategies and tactics to use that work better than older strategies. After a patient or a population of patients has already started a care plan, new information may become available that is relevant to a patient's care plan or to multiple patients' care plans. Health care professionals would want to present that new information to the population of patients impacted in the most efficient way possible, without interrupting their current care plan experiences, or restarting a care plan from scratch.

The present application provides a new and improved method and apparatus for the addition of new content into an already existing care plan for patients, which overcomes the above-referenced problems and others.

In accordance with one aspect, A medical health care network is provided. the network includes at least one server connectable to a communications network. At least one user interface device communicates periodically with the server over the communications network. Content is encoded into a care plan design template that is able to indicate whether content is a replacement or supplement for other content.

In accordance with another aspect, a method of updating a health care network is provided. At least one server is connected to at least one user interface device over a communications link. The network provides personal health care programming to at least one patient, but is capable of serving many patients. A care plan is prescribed to the at least one patient and content elements are assigned for presentation to the at least one patient associated with the care plan. Programming is updated for the at least one patient by substantially seamlessly substituting updated content elements for currently implemented content elements.

In accordance with another aspect, a medical healthcare network is provided. At least one server is connected to a communications network. At least one user interface device communicates periodically with the server over the communications network. A care plan scheduler distributes replacement content to the at least one user interface device by identifying appropriate content substitutions, removing old content, and adding new content without disrupting an existing care plan experience of a patient or population of patients.

In accordance with another aspect, a medical healthcare network is provided. At least one server connects to a communications network. At least one user interface device communicates periodically with the server over the communications network. At least one database interprets patient results collected in response to prescribed content and patient results from various older content versions to determine a value of the prescribed content relative to the older content versions.

In accordance with another aspect, a video content element for addition to patient care plans to update, supplement, or replace one or more prior content elements is provided. The video content element includes a series of video clips to be presented periodically to a patient. A computer readable coding maps the video clips to video clips of the one or more prior content elements.

One advantage is that it avoids the population segment of patients impacted from having to start their care plan over from the beginning, or having any other type of disruption to their care.

Another advantage lies in automated, yet adaptive and seamless care.

Another advantage is that it adds new content to the future schedule without interrupting the delivery of existing content (unless cancellation of such content is desired).

Another advantage is that it avoids having to provide the patient with new hardware.

Another advantage is that a patient's status in a clinical user interface stays intact.

Another advantage is that the care experience is made easier for the nursing staff that cares for the patients.

Another advantage is that labor cost is saved and standards of care are maintained.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
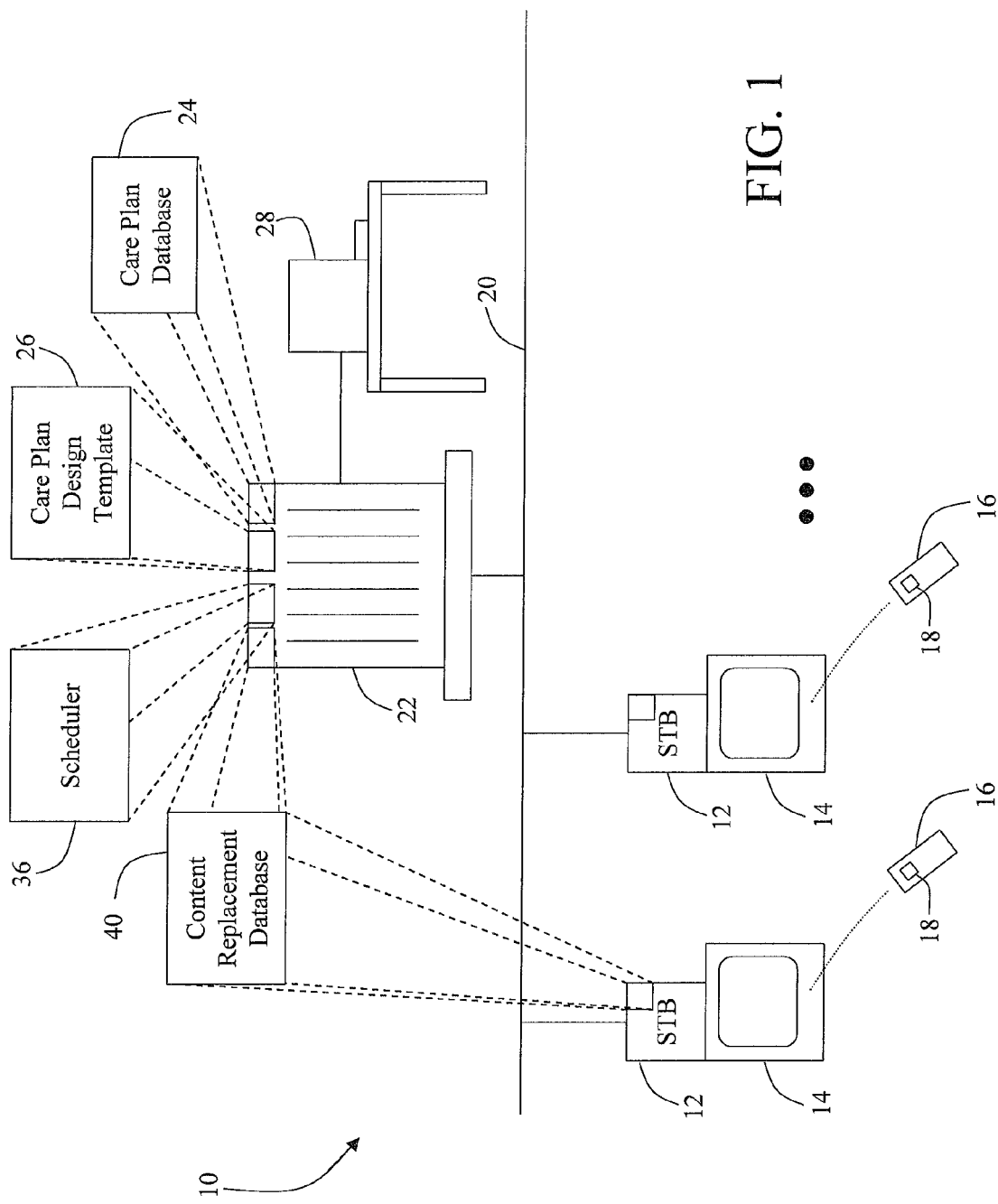
FIG. 1 is an illustration of a patient health care network.

With reference to FIG. 1, a health care network 10 is illustrated. When physicians prescribe short term care such as a finite amount of prescription drugs, rest, and the like, once the patient takes all the pills, etc., the treatment is complete. In many situations, however, the patient is diagnosed with a long term illness or chronic condition that can require long term care and/or lifestyle changes. In this type of situation, the healthcare professional may prescribe habits or behaviors that were not previously a part of the patient's daily regimen. The patient, motivated by his or her visit with the doctor, may start out with this new treatment with the best intentions, but as time lapses, it is easy to slip back into old habits. For instance, a patient may go to his doctor and be diagnosed with diabetes. The doctor recommends that the patient eat better, exercise more, and check his blood sugar levels regularly. Motivated by the newly perceived risk to his health, the patient goes on a diet and exercises. As time goes on, however, the patient starts to lapse back into his old behaviors, and eventually forgets diet and exercise, and possibly regular blood sugar checks. The healthcare network 10 is designed to help keep chronic care patients motivated by providing a dynamic care giving experience even long after any given visit to a doctor and to provide health related feedback from the patient to the caregiver.

Care plans are the fundamental elements in this type of ongoing care. Care plans are patient-specific assemblies of media content elements to affect and maintain changes in patient behavior. As health care professionals put the care plans into use, and then study the results, the professionals are learning about administering the care plan as the patients are learning about their condition from the care plan. The health care professionals learn better ways to tailor care plans by adjusting content, pace, incentives, and other care plan elements to maximize the plan's effect. There is a constant desire to refine and improve the care plan in order to continually improve the quality of care that is administered.

From the health care professionals' point of view, there is a desire to implement new content with minimal disruption to the provision of care. As changes in the care plans are propagated, it is desired that they be developed and implemented in a manner that causes minimal interruption to the experience of the patient. For a care plan designer, it is desired that content versions that were previously used still be available for comparison to subsequent care plans, or for continuing use, if appropriate.

The healthcare network 10 includes a plurality of individual user interface devices 12, such as a set top box, processor or other such interface device which is associated with a display 14, such as a user's television set, monitor or other display device. The patient logs onto the network 10 by using the interface device 12. The interface 12 may be a separate set top box, or may be integrated into the display 14 itself. The interface device 12 also interacts with an input device 16, such as a handheld remote, touchscreen, keyboard, mouse, or other similar device through which the patient can enter information, such as passwords, responses to questionnaires, health related readings such as weight or blood pressure, and the like. The input device 16 includes at least one key 18, but in another embodiment includes a plurality of keys. The input device 16 is preferred to have large keys with distinct markings such as color, shape, and/or labeling that clearly delineate their intended use or functionality.

The interface devices 12 connect or interface with a public or private network 20, such as an interactive cable TV network, the internet, or the like. Although acting over a public network 20, the user interface device 12 communicates over a secure layer of that network 20 to protect sensitive information of the patients. Through the public network 20, the interface device 12 communicates with various servers such as a local server 22. The server 22 includes a look-up-table or database 24 of patient care plans. This database 24 houses the care plans that have been synthesized for all the patients in the network 10 for which this particular server 22 is responsible. A care plan is preferably synthesized by a nurse manager or other health care professional based on the patient's medical history. To create a care plan, the health care professional reviews the patient's medical history, and inputs information to a generic care plan design template 26. The health care professional inputs the information to the template via a user interface 28 with the server 22. The templates 26 act as road maps to direct the health care professional in developing the care plan, ensuring that all appropriate questions are addressed. In addition to the template 26, the health care professional can add features to the care plan based on physician's notes, personality traits of the patient, etc. to further tailor each care plan to an individual patient.

Based on the care plan template 26, the server 22 compiles a care plan for the patient. The server 22 selects the specific content elements (videos, surveys, still pictures, audio files, requests for patient input, etc.) that will be a part of the patient's care plan. The server 22 also decides in what general order the content should be presented to the patient. The server 22 is in periodic communication with the set top box 12 of a particular patient. On an ongoing basis, the server 22 receives information and feedback about the patient's progression through the prescribed material, and selects new content elements for presentation to the patient as they become appropriate. For example, a diabetic will receive general and overview information about diabetes at first, and as the patient progresses through that material, the server 22 will select more detailed and specific content more directed to the particular patient based both on the care plan template 26 and progress and understanding of the patient.

Figure 2:
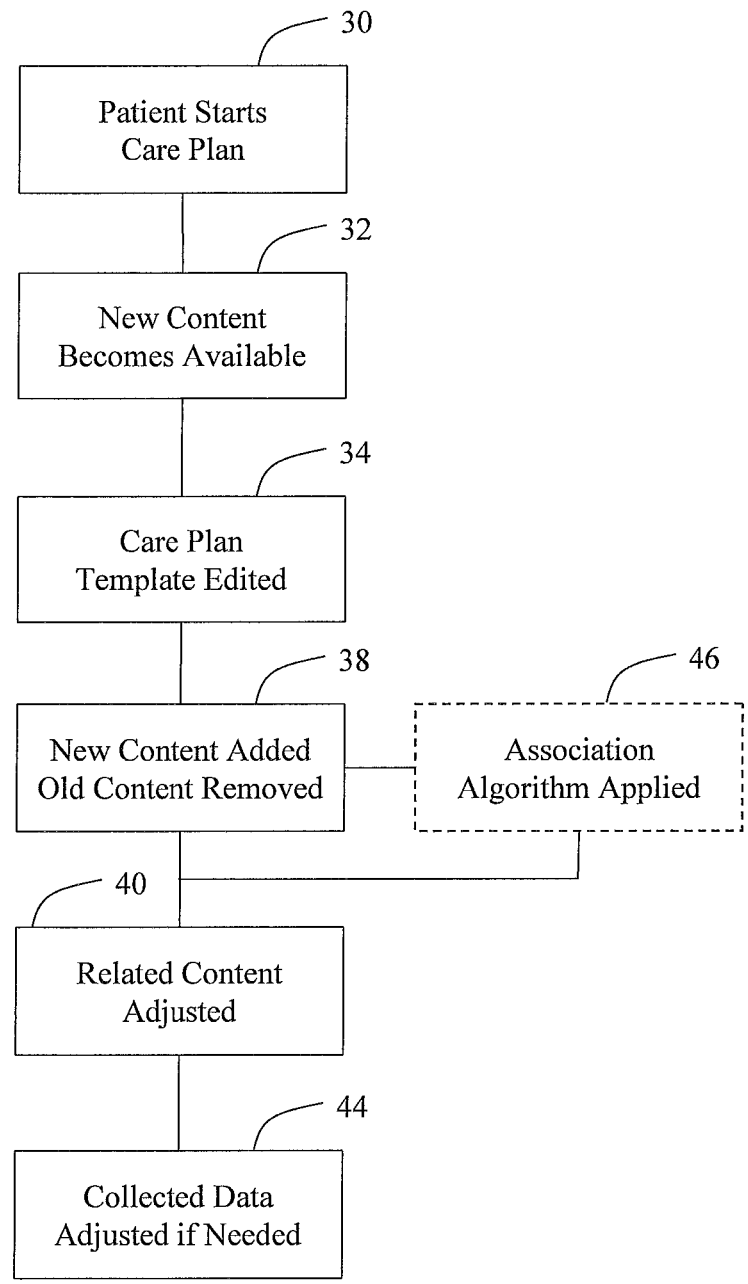
FIG. 2 is a flowchart that depicts the process of replacing content in a patient's care plan.

With reference to FIG. 2, and continuing reference to FIG. 1, once the patient has been issued a set top box 12 and a care plan has been constructed for them, the patient commences the care plan in step 30. As noted in the discussion above, new health care information becomes available (step 32) as the patient progresses through his or her care plan. In order for this new content to be enabled, the care plan template 24 is edited in step 34. This can be done at an administrative level so that all of the servers 22 on the network 10 are aware of the new content. Administrative level changes save labor costs because a care plan designer can make a change to a care plan, and that change can be propagated to all the patients on that care plan. This saves each nurse from having to make the change manually for each patient the change applies to. Additionally, clinical standards of care are maintained because the managers of the service do not need to worry that certain nurses will not implement the desired patient care changes. The changes are made centrally by the care plan designer and then propagated to the patients' care plans directly, effectively by-passing the staff members who are directly responsible for day-to-day management of the patient.

In another embodiment, the care plan template of a single server 22 could be edited, or further, in some but not all servers 22. Further, plans of individual patients may be edited. In addition to adding the new content element, the server 22 also makes a note that the new content is replacing a certain type of old content. To illustrate, say patients with coronary disease watch a "comprehensive coronary disease" video at the start of their care plan. It is decided that this video is far too technical for an introductory video. Health care professionals agree that, instead, the patients should view an "intro to coronary disease" video at the start of their care plans. The second video would be substituted for the first video, but the care plan template would note the substitution. Keeping track of what content elements have been substituted for other content elements is important for later operations.

After the care plan template 26 is updated, each patient's individual care plan must then be updated. Generally, a scheduler 36, in step 38, goes through each patient's care plan looking for the obsolete content and replaces it with the new content. Although the present application largely contemplates replacement of old content with new content, it is to be understood that the care plan template 26 can also be amended such that new content is added, and no content is removed, or vice versa. The replacement step 38 in some instances is that simple, but in other instances it can be more complex. In the simplest case, text can be changed without it having any effect on logical operations. For example, when a spelling error is found in a certain display screen, an administrator corrects the error and updates the care plan template 26. The scheduler 36 then goes through each patient care plan and substitutes the new, correct screen for every instance of the old screen with the spelling error. Another example that would necessitate only a 1 to 1 substitution by the scheduler 36 would be changing the phrasing of a statement or question without changing the content. Certainly, other variations of non-logic changes are contemplated. Again, the scheduler 36 in step 38 would find every instance of the old screen and substitute in the new screen. When a substitution has no logic affecting changes, it is the easiest to implement.

There are, however, more complex situations where it is desirable not to simply replace every instance of old content with the new content. For example, say the care plan template 26 was updated to replace a three-part video on managing lower back pain. The new content element is another three-part video, but it covers the subject matter in a different order. There are several different ways to implement the new video based on the current progress of the patient. The patient may have already completed the old set. The patient might be in the midst of watching the three-part video set. Lastly, the patient might not have started to view the video set.

The easiest one of these situations to handle is the situation where the patient is scheduled to watch the video, but has not yet started. In this situation, the scheduler 36 would review the patient's care plan and note that the patient had not yet started the old video. In this case, the scheduler 36 will substitute in the new video for the old one without the patient's knowledge. The patient had not yet started the old video, so it makes no difference to them that they will be viewing updated content instead of the old, first scheduled content. Although a video is used as an example, any content element (e.g., a survey, literature, an interactive game, and the like) can be replaced without the patient's knowledge if they have not encountered the old content element yet.

Another situation, carrying on the three-part video example, is if the patient has already completed the old content. Here, the scheduler 36 has several options. Its first option would be to do nothing. If the patient has already completed the old content, then there might not be any reason to make the patient aware of the new content if it is largely duplicative of the old content. Another option would be to schedule only those portions that are new. Another option would be to schedule the new content into the patient's care plan. In this situation, the scheduler 36 would weigh the value of the differences between the old and new content elements against disrupting the patient's current schedule. If substantial changes have been made to the new video, it may be worth it to have the patient watch the new video in addition to the old video. This option comes at the expense of delaying other content. In another embodiment, the scheduler 36 would not schedule the video in to the patient's care plan, but rather the scheduler 36 would make it available to the patient if they wanted to review it later on their own time. In this embodiment, the scheduler 36 would instruct the user interface device 12 to give a message to the patient informing them that the new content is available. Then the patient, at their leisure, would be able to access the new content from the menu. When a new or revised video set is designed, the designer typically is familiar with the old video set and knows which information has been added, changed, or deleted. The designer can then code a correlation between the two versions to provide instructions regarding transition points or mapping that will minimize or prevent subject matter from being lost. In some instances, a special transition video may be provided to transition between the two sets at selected points. Other parameters can similarly be coded into the video series or other elements of the care plan to facilitate seamless transitioning.

The last scenario, carrying on the three-part video example, is if the patient is in the midst of watching the video content. In the example, the scheduler 36 determines what topics the patient has already covered in their progress of watching the old video set. Based on that determination, the scheduler makes a decision as to what, if any, of the new video set is substituted into the patient's care plan. If the topics are taken in the same order, then the scheduler 36 may make a substitution of the unseen portion or portions. If the topics within the video set are taken in a different order, the scheduler 36 may cancel the rest of the old content and start the patient watching the new content in its entirety. In another embodiment, the scheduler 36 allows the patient to finish the old set of videos. In any of these embodiments, the scheduler 36 can make both the new content and the old content available to the patient to review on their own time. Again, the scheduler 36 weighs the value of viewing the new content against the burden of delaying other content in the patient's care plan.

When new content is added, or old content removed, etc., there are sometimes other events that are affected by the change. For example, a patient is given the option to watch video "A" now, or save it for later. If the patient saves it for later, in one embodiment, the user interface device will display a reminder to watch video "A" periodically, until the patient watches video "A". If, before the patient watches the video, the video is removed or replaced, the scheduler 36 also removes the reminder message. More generally this can be applied to any content element. When a content element in a care plan changes, the scheduler 36 finds all of the related elements in step 40 (messages, reminders, surveys, and the like) and disposes of them accordingly. There may be instances that these associated elements can be retroactively associated with a replacement content element. In other situations, it is best to remove the associated elements and replace them with new ones.

Also if content is delayed, associated elements should also be delayed. In the above example of the three-part video on managing back pain, perhaps the health care professional decides that it is best for the patient to view both the old and the new videos. If a survey was scheduled for after the video, it now may be delayed until after the patient watches both videos. The scheduler 36 generally decides what content will be affected and where in the care plan are logical points for affected content, subject to being overridden by the health care professional.

In the above described embodiments, the scheduler 36 determines when and if the patient views the new content instead of the old content. It is to be understood that this decision can be overridden by a healthcare professional managing the patient's care plan. The health care professional may know more information that the scheduler 36 cannot assimilate, or has not yet assimilated. For instance, where two patients are in similar care plans, the health care professional may know that one patient would not mind watching a second video in addition to a first one; whereas, the other patient will just get frustrated if they are instructed to watch a second video covering substantially similar topics. The health care professional might allow the scheduler to amend the first patient's care plan, but override the second, so that patient can continue on directly to subsequent material.

The examples above illustrate the global substitution of old content for new content. That is, there is a better video, and it will benefit all patients to whom it pertains. Patient specific substitutions are also contemplated. For instance, alternative videos may exist, and one is thought to be the best among them, but as to a specific patient, they might respond to one of the alternatives better, and the health care professional can make those decisions on a patient by patient basis. Additionally, the health care professional can add ad-hoc content elements to which they think the patient would respond well.

After the scheduler 36 makes the content substitution, there still may be issues as to whether the new content element meshes well into the patient's care plan. A content replacement database 42 translates data collected under the old content to match data collected under the updated content in step 44. This prevents old data, previously collected from the patient, from appearing aberrant in the context of the new content. For example, suppose that the patient is asked, every morning, to report how well they slept the night before on a scale from 1 to 10. The patient does this for a period of time. Subsequently, health care professionals decide that they could receive more accurate information if the patient reported how well they slept on a scale from 1 to 20. This new questionnaire is then substituted into the patient's care plan. The patient dutifully answers this new questionnaire for a period of time. Some time later, a health care professional wants to chart the patient's ability to sleep over the time that the patient has been using the care plan. The professional discovers that the patient's ability to sleep spiked from below average (8 or 9) to very good (16 or 17) right around the time the new questionnaire was implemented.

As it can be seen, there was actually no change in the patient's sleeping habits, just old data being used in a new frame of reference. The content replacement database 40 monitors when content is replaced, and scales collected data accordingly, avoiding potentially misleading results such as the conclusion reached above. The content replacement database 40 can be located in the user interface device 12. In this embodiment, data is scaled before it is reported back to the server 22, or notation is made to scale data already sent to the server 22. In another embodiment, the content replacement database can be located in the server 22. In this embodiment, the content replacement database 40 would monitor all care plans administered by that server 22 instead of only one care plan. The content replacement database ensures that when a content element is changed, data is reported to the health care professional in a meaningful and accurate manner.

Additionally, historical data can have additional value over and above that which is previously discussed. In particular, another reason to keep old data is to compare it to new data to determined the effectiveness of new content, new treatments, and the like. This comparison can be done to postulate conclusions about the patient pool in general, or sub-classes of patients. For example, reports can be generated to compare efficacy of two or more series of videos or other care plan modules for helping a patient achieve a designated goal, such as stopping smoking or losing weight.

In another example, perhaps a patient is asked to respond to a daily survey that has three options. On a certain date, that survey is replaced with one that has four response options. The content replacement database 40 would make a note in the collected data that explains why the patient never picked the fourth option before the certain date. Again, the content replacement database 40 ensures that otherwise useful data will not be misinterpreted simply because a content element has been modified.

On occasion, it may be necessary to substitute an entirely new care plan for an existing care plan. In this type of situation, an association algorithm is developed to associate the old and the new care plans. In step 46 the scheduler 36 analyzes the patient's progress through the old care plan and applies the association algorithm. After the algorithm is run, the scheduler 36 has determined the most logical point for the patient to start within the new care plan. The association algorithm can consider a multitude of factors, including, but not limited to, age of the patient, the patient's grasp of the material thus far, the point in the old care plan where the patient left off, the patient's rate of progression through the old care plan, and the like.

The above examples are only illustrative of the possible modifications to the care plan that can be effected. Other changes are certainly contemplated. Other illustrative examples of changes contemplated to care plans are changing the phrasing of a question on a survey, changing the phrasing of a message, adding an answer option to a survey, changing how a survey branches, changing how a survey is scored, adding a new task for a certain response to a survey, adding a new survey to the care plan, adding a new survey to the library for ad-hoc scheduling, adding a message/tip to a care plan, changing the order of content, changing logic or content within goal modules, conditional scheduling based on survey responses, changing scoring of vital rules, changing the logic of vital rules, changing how a script branches, changing a care plan's scheduling of elements, adding videos to care plans, and the like. This list is only exemplary, and not intended to be an exhaustive list of possible modifications or additions to care plans.

In addition to new content being made available for patients, the clinical user interface (CUI) can be changed or improved. Pull down menus can be added, pull down menus can be changed by adding, deleting, or changing the items within the menu, labels can be changed, and data fields can be changed. These changes change how the health care professional develops a care plan, tailoring it to an individual patient, but these changes should not affect existing care plans, unless the health care professional subsequently modifies the existing care plan using the new CUI.

In summary, when new content becomes available, a health care professional modifies a care plan template 26 to include the new content instead of the old content. A scheduler 36 looks through each patient's care plan for the old content and replaces it with the new content in the least disturbing way possible, if possible, without the patient even knowing something was changed. A content replacement database 40 correlates old data with new data to ensure that new content meshes well into the patient's care plan and feedback procured therefrom.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A medical health care network comprising:
   at least one server connectable to a communications network;
   at least one user interface device that communicates periodically with the server over the communications network; and
   a care plan design template into which one or more specific content elements are encoded, via the user interface device, for presentation to a patient, the care plan design template comprising a care plan for the patient;
   wherein the care plan design template is configured to be edited to add new content, the editing including at least one of,
      new replacement content inserted into the care plan design template that may be presented as a replacement for at least one of the one or more specific content elements previously encoded into the care plan design template, and
      new supplemental content inserted into the care plan design template that may be presented in addition to at least one of the one or more specific content elements previously encoded into the care plan design template,
   wherein the care plan design template further includes a first indication when the new content is new replacement content and a second indication when the new content is new supplemental content,
   wherein the at least one server determines that new replacement content should be scheduled for presentation to the patient depending on a first progression of the patient through the one or more specific content elements and that the new supplemental content should be scheduled for presentation to the patient depending on a second progression of the patient through the one or more specific content elements.

2. The medical health care network as set forth in claim 1, further including:
   a patient interface device; and
   a care plan scheduler that distributes new content to the patient interface device.

3. The medical health care network as set forth in claim 2, wherein the care plan scheduler is located in the at least one server.

4. The medical health care network as set forth in claim 1, further including:
   a content replacement database that integrates the new content into care plans scheduled for presentation to the patient.

5. The medical health care network as set forth in claim 4, wherein the content replacement database is located in the at least one user interface device.

6. The medical health care network as set forth in claim 4, wherein the content replacement database is located in the at least one server.

7. The medical health care network as set forth in claim 1, further including:
   a patient interface device;
   a care plan scheduler that distributes new content to the patient interface device; and,
   a content replacement database that integrates the new content into care plans scheduled for presentation to the patient.

8. The medical health care network as set forth in claim 1, wherein the care plan design template is located in the at least one server.

9. The medical healthcare network of claim 1, further comprising:
   at least one database that interprets patient results collected in response to the new content and patient results from the one or more specific content elements previously encoded into the care plan design template to determine a value of the new content relative to the one or more specific content elements previously encoded into the care plan design template.

10. A method, comprising:
    encoding, via a user interface device, one or more specific content elements to a care plan design template for presentation to a patient, the care plan design template comprising a care plan for the patient;
    editing, via the user interface device, the care plan design template to add new content, the editing including at least one of,
       inserting new replacement content into the care plan design template that may be presented as a replacement for at least one of the one or more specific content elements previously encoded into the care plan design template, wherein the care plan design template further includes a first indication that the new content is new replacement content, and
       inserting new supplemental content into the care plan design template that may be presented in addition to at least one of the one or more specific content elements previously encoded into the care plan design template, wherein the care plan design template further includes a second indication that the new content is new supplemental content;
    determining, by a server device, that new replacement content should be scheduled for presentation to the patient depending on a first progression of the patient through the one or more specific content elements; and
    determining, by the server device, that the new supplemental content should be scheduled for presentation to the patient depending on a second progression of the patient through the one or more specific content elements.

11. The method of claim 10, further comprising:
    distributing the new content to a patient interface device.

12. The method of claim 10, further comprising:
    integrating the new content into care plans scheduled for presentation to the patient.

13. The method of claim 10, further comprising:
    interpreting patient results collected in response to the new content and patient results from the one or more specific content elements previously encoded into the care plan design template to determine a value of the new content relative to the one or more specific content elements previously encoded into the care plan design template.

* * * * *